(12) United States Patent
Kumon et al.

(10) Patent No.: US 8,658,612 B2
(45) Date of Patent: Feb. 25, 2014

(54) THERAPEUTIC AGENT FOR MALIGNANT MESOTHELIOMA AND IMMUNOSTIMULANT

(75) Inventors: Hiromi Kumon, Okayama (JP); Yasutomo Nasu, Okayama (JP); Yuji Kashiwakura, Okayama (JP); Masami Watanabe, Okayama (JP); Nam-ho Huh, Okayama (JP); Masakiyo Sakaguchi, Okayama (JP)

(73) Assignees: National University Corporation Okayama University, Okayama-shi, Okayama (JP); Momotaro-Gene Inc., Okayama-shi, Okayama (JP)

( * ) Notice: Subject to any disclaimer, the term of this patent is extended or adjusted under 35 U.S.C. 154(b) by 0 days.

(21) Appl. No.: 13/056,443

(22) PCT Filed: Jul. 30, 2009

(86) PCT No.: PCT/JP2009/063907
§ 371 (c)(1),
(2), (4) Date: Mar. 11, 2011

(87) PCT Pub. No.: WO2010/013846
PCT Pub. Date: Feb. 4, 2010

(65) Prior Publication Data
US 2011/0189237 A1    Aug. 4, 2011

(30) Foreign Application Priority Data

Jul. 30, 2008 (JP) ................................. 2008-196857

(51) Int. Cl.
*A01N 43/04* (2006.01)
*C12N 15/00* (2006.01)
*C12N 15/63* (2006.01)
*C07H 21/04* (2006.01)

(52) U.S. Cl.
USPC .......... 514/44; 435/320.1; 435/455; 536/23.5

(58) Field of Classification Search
USPC .................. 435/320.1, 455; 514/44; 536/23.5
See application file for complete search history.

(56) References Cited

U.S. PATENT DOCUMENTS

| 7,314,627 | B2 * | 1/2008 | Haynes et al. ............ 424/196.11 |
| 2009/0005538 | A1 | 1/2009 | Kumon et al. |
| 2010/0173404 | A1 | 7/2010 | Kumon et al. |
| 2010/0204308 | A1 | 8/2010 | Namba et al. |
| 2011/0166545 | A1 | 7/2011 | Kumon et al. |

FOREIGN PATENT DOCUMENTS

| WO | WO 01/38523 A1 | 5/2001 |
| WO | WO2006/098074 A1 | 9/2006 |
| WO | 2008/050898 A1 | 5/2008 |

OTHER PUBLICATIONS

Kumon et al., 2006, Geneseq Accession No. AEK54773, computer printout, pp. 3-5.*
McCluskie et al., 1999, Molecular Medicine, vol. 5, p. 287-300.*
Massa et al., 2008, Human Gene Therapy, vol. 19, p. 354-364.*
Zhang et al., 2006, Expert rev. Vaccine, vol. 5, No. 2, p. 223-231.*
Tollefsen et al., 2003, Scandinavian Journal of Immunology, vol. 57, p. 229-238.*
Skolnick et al., 2000, Trends in Biotech, vol. 18, p. 34-39.*
Tomasinsig et al., 2005, Current Protein and Peptide Science, vol. 6, p. 23-34.*
Smallwood et al., 2002,, Virology, vol. 304, p. 135-145.*
Chattopadhyay et al., 2004, Virus Research, vol. 99, p. 139-145.*
Abarzua, Fernando et al., "Adenovirus-Medicated Overexpression of REIC/Dkk-3 Selectively Induces Apoptosis in Human Prostate Cancer Cells through Activation of c-Jun-$NH_2$-Kinase", Cancer Research, 2005, vol. 65, No. 21, pp. 9617-9622.
Tanimoto, Ryuta et al., "REIC/Dkk-3 as a potential gene therapeutic agent against human testicular cancer", International Journal of Molecular Medicine, 2007, vol. 19, pp. 363-368.
Abarzua, Fernando et al., "Heat shock proteins play a crucial role in tumor-specific apoptosis by REIC/Dkk-3", International Journal of Molecular Medicine, 2007, vol. 20, pp. 37-43.
Edamura, K. et al., "Adenovirus-medicated REIC/Dkk-3 gene transfer inhibits tumor growth and metastasis in an orthotopic prostate cancel model", Cancer Gene Therapy, 2007, vol. 14, No. 9, pp. 765-772.
International Search Report dated Nov. 17, 2009 corresponding with International Application No. PCT/JP2009/063907 (English).
PCT International Preliminary Examination Report dated Nov. 5, 2009 in PCT/JP2009/063907.
Kashiwakura et al., "Adenovirus-mediated REIC/Dkk-3 gene transfer prevented mesothelioma tumor progressions in orthotopic mice model", Journal of Gene Medicine, vol. 10, No. 4, 67, Apr. 15, 2008, pp. 469-470.
European Search Report dated Feb. 6, 2012, issued in corresponding European Application No. 09803076.0.
Xianfei et al., "Effects of c-Jun N-terminal kinase signaling transduction on cell apoptosis," J. Fourth Mil. Med. Univ., vol. 26, No. 16, Dec. 31, 2005, pp. 1533-1534.
GenBank Accession No. AY587550, version AY587550.1, "Homo sapiens putative tumor suppressor Dkk-3/REIC (DKK3) mRNA, complete cds"; Dec. 17, 2004; accessed online at: http://www.ncbi.nlm.nih.gov/nuccore/AY587550; 2 pages. entire document.
Office Action, dated Sep. 24, 2012, and English translation, issued in CN Application No. 200980136054.8.

* cited by examiner

*Primary Examiner* — Shin-Lin Chen
(74) *Attorney, Agent, or Firm* — Fitch Even Tabin & Flannery LLP

(57) ABSTRACT

A method for potentiating the antitumor immunity in an animal by administering REIC/Dkk-3, or a therapeutic agent for malignant mesothelioma containing REIC/Dkk-3, or a vector containing the DNA as an active ingredient; wherein the DNA consists of the nucleotide sequence shown in SEQ ID NO: 1; or (b) a DNA hybridizing under stringent conditions to the DNA consisting of a nucleotide sequence complementary to the nucleotide sequence shown in SEQ ID NO: 1 and encoding a protein having apoptosis-inducing activity and interleukin (IL-7) production-accelerating activity in cells.

3 Claims, 18 Drawing Sheets
(12 of 18 Drawing Sheet(s) Filed in Color)

bar = 50 μm

Intratumoral

SEQUENCE LISTING

```
<160> NUMBER OF SEQ ID NOS: 2

<210> SEQ ID NO 1
<211> LENGTH: 1053
<212> TYPE: DNA
<213> ORGANISM: Homo sapiens
<220> FEATURE:
<221> NAME/KEY: CDS
<222> LOCATION: (1)..(1050)

<400> SEQUENCE: 1 atg cag cgg ctt ggg gcc acc ctg ctg tgc ctg cta ctg gcg gcg gcg      48
Met Gln Arg Leu Gly Ala Thr Leu Leu Cys Leu Leu Leu Ala Ala Ala
1               5                   10                  15 gtc ccc acg gcc ccc gcg ccc gct ccg acg gcg acc tcg gct cca gtc      96
Val Pro Thr Ala Pro Ala Pro Ala Pro Thr Ala Thr Ser Ala Pro Val
                20                  25                  30 aag ccc ggc ccg gct ctc agc tac ccg cag gag gag gcc acc ctc aat     144
Lys Pro Gly Pro Ala Leu Ser Tyr Pro Gln Glu Glu Ala Thr Leu Asn
            35                  40                  45 gag atg ttc cgc gag gtt gag gaa ctg gtg gag gac acg cag cac aaa     192
Glu Met Phe Arg Glu Val Glu Glu Leu Val Glu Asp Thr Gln His Lys
        50                  55                  60 ttg cgc agc gcg gtg gaa gag atg gag gca gaa gaa gct gct gct aaa     240
Leu Arg Ser Ala Val Glu Glu Met Glu Ala Glu Glu Ala Ala Ala Lys
65                  70                  75                  80 gca tca tca gaa gtg aac ctg gca aac tta cct ccc agc tat cac aat     288
Ala Ser Ser Glu Val Asn Leu Ala Asn Leu Pro Pro Ser Tyr His Asn
                85                  90                  95 gag acc aac aca gac acg aag gtt gga aat aat acc atc cat gtg cac     336
Glu Thr Asn Thr Asp Thr Lys Val Gly Asn Asn Thr Ile His Val His
                100                 105                 110 cga gaa att cac aag ata acc aac aac cag gct cga caa atg gtc ttt     384
Arg Glu Ile His Lys Ile Thr Asn Asn Gln Ala Arg Gln Met Val Phe
            115                 120                 125 tca gag aca gtt atc aca tct gtg gga gac gaa gaa ggc aga agg agc     432
Ser Glu Thr Val Ile Thr Ser Val Gly Asp Glu Glu Gly Arg Arg Ser
        130                 135                 140 cac gag tgc atc atc gac gag gac tgt ggg ccc agc atg tac tgc cag     480
His Glu Cys Ile Ile Asp Glu Asp Cys Gly Pro Ser Met Tyr Cys Gln
145                 150                 155                 160 ttt gcc agc ttc cag tac acc tgc cag cca tgc cgg ggc cag agg atg     528
Phe Ala Ser Phe Gln Tyr Thr Cys Gln Pro Cys Arg Gly Gln Arg Met
```

```
                     165                 170                 175
ctc tgc acc cgg gac agt gag tgc tgt gga gac cag ctg tgt gtc tgg      576
Leu Cys Thr Arg Asp Ser Glu Cys Cys Gly Asp Gln Leu Cys Val Trp
            180                 185                 190 ggt cac tgc acc aaa atg gcc acc agg ggc agc aat ggg acc atc tgt      624
Gly His Cys Thr Lys Met Ala Thr Arg Gly Ser Asn Gly Thr Ile Cys
        195                 200                 205 gac aac cag agg gac tgc cag ccg ggg ctg tgt tgt gcc ttc cag aga      672
Asp Asn Gln Arg Asp Cys Gln Pro Gly Leu Cys Cys Ala Phe Gln Arg
    210                 215                 220 ggc ctg ctg ttc cct gtg tgc ata ccc ctg ccc gtg gag ggc gag ctt      720
Gly Leu Leu Phe Pro Val Cys Ile Pro Leu Pro Val Glu Gly Glu Leu
225                 230                 235                 240 tgc cat gac ccc gcc agc cgg ctt ctg gac ctc atc acc tgg gag cta      768
Cys His Asp Pro Ala Ser Arg Leu Leu Asp Leu Ile Thr Trp Glu Leu
                245                 250                 255 gag cct gat gga gcc ttg gac cga tgc cct tgt gcc agt ggc ctc ctc      816
Glu Pro Asp Gly Ala Leu Asp Arg Cys Pro Cys Ala Ser Gly Leu Leu
            260                 265                 270 tgc cag ccc cac agc cac agc ctg gtg tat gtg tgc aag ccg acc ttc      864
Cys Gln Pro His Ser His Ser Leu Val Tyr Val Cys Lys Pro Thr Phe
        275                 280                 285 gtg ggg agc cgt gac caa gat ggg gag atc ctg ctg ccc aga gag gtc      912
Val Gly Ser Arg Asp Gln Asp Gly Glu Ile Leu Leu Pro Arg Glu Val
    290                 295                 300 ccc gat gag tat gaa gtt ggc agc ttc atg gag gag gtg cgc cag gag      960
Pro Asp Glu Tyr Glu Val Gly Ser Phe Met Glu Glu Val Arg Gln Glu
305                 310                 315                 320 ctg gag gac ctg gag agg agc ctg act gaa gag atg gcg ctg ggg gag     1008
Leu Glu Asp Leu Glu Arg Ser Leu Thr Glu Glu Met Ala Leu Gly Glu
                325                 330                 335 cct gcg gct gcc gcc gct gca ctg ctg gga ggg gaa gag att tag         1053
Pro Ala Ala Ala Ala Ala Leu Leu Gly Gly Glu Glu Ile
            340                 345                 350

<210> SEQ ID NO 2
<211> LENGTH: 350
<212> TYPE: PRT
<213> ORGANISM: Homo sapiens

<400> SEQUENCE: 2

Met Gln Arg Leu Gly Ala Thr Leu Leu Cys Leu Leu Leu Ala Ala
1               5                   10                  15

Val Pro Thr Ala Pro Ala Pro Ala Pro Thr Ala Thr Ser Ala Pro Val
                20                  25                  30

Lys Pro Gly Pro Ala Leu Ser Tyr Pro Gln Glu Glu Ala Thr Leu Asn
            35                  40                  45

Glu Met Phe Arg Glu Val Glu Glu Leu Val Glu Asp Thr Gln His Lys
    50                  55                  60

Leu Arg Ser Ala Val Glu Glu Met Glu Ala Glu Ala Ala Lys
65                  70                  75                  80

Ala Ser Ser Glu Val Asn Leu Ala Asn Leu Pro Pro Ser Tyr His Asn
                85                  90                  95

Glu Thr Asn Thr Asp Thr Lys Val Gly Asn Asn Thr Ile His Val His
            100                 105                 110

Arg Glu Ile His Lys Ile Thr Asn Asn Gln Ala Arg Gln Met Val Phe
    115                 120                 125

Ser Glu Thr Val Ile Thr Ser Val Gly Asp Glu Glu Gly Arg Arg Ser
130                 135                 140
```

-continued

```
His Glu Cys Ile Ile Asp Glu Asp Cys Gly Pro Ser Met Tyr Cys Gln
145                 150                 155                 160

Phe Ala Ser Phe Gln Tyr Thr Cys Gln Pro Cys Arg Gly Gln Arg Met
                165                 170                 175

Leu Cys Thr Arg Asp Ser Glu Cys Cys Gly Asp Gln Leu Cys Val Trp
            180                 185                 190

Gly His Cys Thr Lys Met Ala Thr Arg Gly Ser Asn Gly Thr Ile Cys
        195                 200                 205

Asp Asn Gln Arg Asp Cys Gln Pro Gly Leu Cys Cys Ala Phe Gln Arg
    210                 215                 220

Gly Leu Leu Phe Pro Val Cys Ile Pro Leu Pro Val Glu Gly Glu Leu
225                 230                 235                 240

Cys His Asp Pro Ala Ser Arg Leu Leu Asp Leu Ile Thr Trp Glu Leu
                245                 250                 255

Glu Pro Asp Gly Ala Leu Asp Arg Cys Pro Cys Ala Ser Gly Leu Leu
            260                 265                 270

Cys Gln Pro His Ser His Ser Leu Val Tyr Val Cys Lys Pro Thr Phe
        275                 280                 285

Val Gly Ser Arg Asp Gln Asp Gly Glu Ile Leu Leu Pro Arg Glu Val
    290                 295                 300

Pro Asp Glu Tyr Glu Val Gly Ser Phe Met Glu Glu Val Arg Gln Glu
305                 310                 315                 320

Leu Glu Asp Leu Glu Arg Ser Leu Thr Glu Glu Met Ala Leu Gly Glu
                325                 330                 335

Pro Ala Ala Ala Ala Ala Leu Leu Gly Gly Glu Glu Ile
                340                 345                 350
```

THERAPEUTIC AGENT FOR MALIGNANT MESOTHELIOMA AND IMMUNOSTIMULANT

CROSS-REFERENCE TO RELATED APPLICATIONS

This is the U.S. National Phase of International Application PCT/JP2009/063907, filed Jul. 30, 2009, and claims priority benefit under 35 U.S.C. §119 based on Japanese Application No. 2008-196857, filed Jul. 30, 2008, the entire disclosures of which applications are hereby incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 27, 2011, is named 81879929.txt and is 8,652 bytes in size.

TECHNICAL FIELD

The present invention relates to a therapeutic agent for malignant mesothelioma and an immunostimulant.

BACKGROUND ART

The lungs in the chest, as well as abdominal organs such as the stomach, the intestines, the liver, and the heart are each wrapped in membranes such as pleura, peritoneum, and pericardium. A portion that covers the surface of such a membrane is referred to as mesothelium. A tumor that is developed from such mesothelium is referred to as a mesothelioma. Mesotheliomas are classified into pleuramesothelioma, peritoneal mesothelioma, pericardial mesothelioma, and the like depending on the primary sites.

Mesotheliomas are also classified into malignant mesothelioma and benign mesothelioma. Malignant mesothelioma is further classified into localized mesothelioma and diffuse mesothelioma. The relationship of pleuramesothelioma and peritoneal mesothelioma with asbestos exposure has been proved. In recent years, mesothelioma has been on the increase.

Conventional treatments for malignant mesothelioma are mainly trimodality treatments using surgical therapy, chemotherapy, and radiotherapy in combination. The 5-year survival rate is still 10% or less, and malignant mesothelioma is an intractable solid cancer.

Surgical therapy includes pleurectomy, pleurolysis, and extrapleural pneumonectomy. However, the former therapy is problematic in terms of curability and the latter therapy is problematic because of its many complications. A variety of chemotherapy regimes have been attempted, including a combination of pemetrexed+CDDP, but they are not always drastically effective and often cause adverse reactions. Radiation therapy merely plays an ancillary role. In recent years, systemic medication with IL-2, IFN-γ, or the like has been attempted as cytokine therapy. However, cytokine therapy causes strong adverse reactions and cytoreductive effects are not obtained to the extent expected. Hence, definite effects cannot be expected from any therapy. The creation of a stronger treatment strategy for malignant mesothelioma is a pressing need.

REIC/Dkk-3 has been identified at Okayama University as a gene whose expression is lowered in association with immortalization of normal human fibroblasts. It was clarified later that REIC/Dkk-3 is homologous to a mammalian gene member of the Dkk (dickkopf) gene family involved in formation of a *Xenopus* head (see International Patent Publication WO01/038523 Pamphlet and Tsuji, T. et al., Biochem-Biophys Res Commun 268, 20-4 (2000)). It has been revealed by examination using a human prostatic cancer-derived cell line that infection with the REIC/Dkk-3 adenovirus (hereinafter, Ad-REIC) results in generation of intracellular stresses, activating c-jun N-terminal Kinase (JNK) and thus inducing apoptosis (see Abarzua et al., Cancer Res. 65, 9617-9255 (2005)).

DISCLOSURE OF THE INVENTION

An object of the present invention is to provide a method for treating malignant mesothelioma using REIC/Dkk-3 and a therapeutic agent for malignant mesothelioma comprising REIC/Dkk-3. Another object of the present invention is to provide a method for potentiating immunity using REIC/Dkk-3 and an immunostimulant comprising REIC/Dkk-3.

The present inventors examined a drastically new therapeutic method for treating malignant mesothelioma. Specifically, when malignant mesothelioma cells (211H, H28, and H2052) were infected in vitro with an adenovirus vector (Ad-REIC) comprising a REIC-Dkk-3 gene, JNK-dependent apoptosis took place. The result demonstrated that JNK-dependent apoptosis occurs due to decreased expression of Id-1 (Inhibition of differentiation-1) deeply involved in cell growth and the like. Such involvement of Id-1 was also confirmed in sympatric malignant mesothelioma model mice. Meanwhile, drastic anti-tumor effects were exerted although gene transfer to tumor cells in vivo did not take place 100%, suggesting possible induction of some immunopotentiating effects by intrapleural administration of Ad-REIC. Hence, analysis was conducted using normal cells (fibroblasts). As a result, it was discovered that in vitro infection of normal fibroblasts with Ad-REIC resulted in enhanced production of IL-7 (cytokine contributing to activation of NK (Natural Killer) cells) from the fibroblasts. Also, it was revealed that the thus enhanced IL-7 production was due to JNK activation→p38 activation→STAT-1 activation→IRF-1 activation. The method performed by the present inventors involving intrapleural administration of a viral vector is very efficient for gene transfer to the pleura. Thus, it is considered that IL-7 production is enhanced also in normal pleural cells due to a similar mechanism, potentiating antitumor immunity in which NK cells are mainly involved.

Based on the above findings, it has been revealed that intrapleural administration of Ad-REIC against malignant mesothelioma exerts drastic therapeutic effects unseen among other therapeutic methods by inducing not only apoptosis in tumor cells, but also antitumor-immunostimulating ability in normal pleural cells.

Treatment of malignant mesothelioma using the therapeutic agent of the present invention has the following characteristics.

1. Direct intrapleural administration of REIC/Dkk-3 adenovirus
2. Induction of cancer cell apoptosis via administered REIC/Dkk-3
3. NK cell activation as a result of enhancement in IL-7 production capability of normal pleural cells via administered REIC/Dkk-3, and potentiation of antitumor immunity The present invention is as follows.

[1] A mesothelioma therapeutic agent comprising the following REIC/Dkk-3 DNA or a vector comprising the DNA as an active ingredient:
(a) a DNA consisting of the nucleotide sequence shown in SEQ ID NO: 1; or
(b) a DNA hybridizing under stringent conditions to a DNA consisting of a nucleotide sequence complementary to the nucleotide sequence shown in SEQ ID NO: 1 and encoding a protein having apoptosis-inducing activity and IL-7 production-accelerating activity in cells.

[2] The mesothelioma therapeutic agent according to [1], wherein the vector is an adenovirus vector.

[3] The mesothelioma therapeutic agent according to [1] or [2], wherein the mesothelioma is pleuramesothelioma.

[4] The mesothelioma therapeutic agent according to [3], which is used for intrapleural administration.

[5] The mesothelioma therapeutic agent according to any one of [1] to [4], which induces apoptosis in tumor cells and potentiates the antitumor immunity of normal cells.

[6] An immunostimulant comprising the following REIC/Dkk-3 DNA or a vector comprising the DNA as an active ingredient:
(a) a DNA consisting of the nucleotide sequence shown in SEQ ID NO: 1; or
(b) a DNA hybridizing under stringent conditions to a DNA consisting of a nucleotide sequence complementary to the nucleotide sequence shown in SEQ ID NO: 1 and encoding a protein having apoptosis-inducing activity and IL-7 production-accelerating activity in cells.

[7] The immunostimulant according to [6], wherein the vector is an adenovirus vector.

[8] A method for treating mesothelioma comprising administering the following REIC/Dkk-3 DNA or a vector comprising the DNA to a mesothelioma patient:
(a) a DNA consisting of the nucleotide sequence shown in SEQ ID NO: 1; or
(b) a DNA hybridizing under stringent conditions to a DNA consisting of a nucleotide sequence complementary to the nucleotide sequence shown in SEQ ID NO: 1 and encoding a protein having apoptosis-inducing activity and IL-7 production accelerating activity in cells.

[9] The method for treating mesothelioma according to [8], wherein the vector is an adenovirus vector.

[10] The method for treating mesothelioma according to [9], wherein the mesothelioma is pleuramesothelioma.

[11] The method for treating mesothelioma according to [10], comprising administering the REIC/Dkk-3 DNA or a vector comprising the DNA intrapleurally.

[12] The method for treating mesothelioma according to [8], comprising inducing apoptosis in tumor cells and potentiating the antitumor immunity of normal cells.

[13] A method for potentiating the antitumor immunity of an animal, comprising administering the following REIC/Dkk-3 DNA or a vector comprising the DNA to an animal:
(a) a DNA consisting of the nucleotide sequence shown in SEQ ID NO: 1; or
(b) a DNA hybridizing under stringent conditions to a DNA consisting of a nucleotide sequence complementary to the nucleotide sequence shown in SEQ ID NO: 1 and encoding a protein having apoptosis-inducing activity and IL-7 production accelerating activity in cells.

[14] The method for potentiating antitumor immunity according to [13], wherein the vector is an adenovirus vector.

[15] Use of the following REIC/Dkk-3 DNA or a vector comprising the DNA for production of a mesothelioma therapeutic agent:
(a) a DNA consisting of the nucleotide sequence shown in SEQ ID NO: 1; or
(b) a DNA hybridizing under stringent conditions to a DNA consisting of a nucleotide sequence complementary to the nucleotide sequence shown in SEQ ID NO: 1 and encoding a protein having apoptosis-inducing activity and IL-7 production accelerating activity in cells.

[16] The use according to [15], wherein the vector is an adenovirus vector.

[17] The use according to [15] or [16], wherein the mesothelioma is pleuramesothelioma.

[18] The use according to [17], comprising intrapleural administration of the REIC/Dkk-3 DNA or a vector comprising the DNA.

[19] The use according to any one of [15] to [18], wherein the mesothelioma therapeutic agent induces apoptosis in tumor cells and potentiates the antitumor immunity of normal cells.

[20] Use of the following REIC/Dkk-3 DNA or a vector comprising the DNA for production of an immunostimulant for an animal:
(a) a DNA consisting of the nucleotide sequence shown in SEQ ID NO: 1; or
(b) a DNA hybridizing under stringent conditions to a DNA consisting of a nucleotide sequence complementary to the nucleotide sequence shown in SEQ ID NO: 1 and encoding a protein having apoptosis-inducing activity and IL-7 production accelerating activity in cells.

[21] The use according to [20], wherein the vector is an adenovirus vector.

[22] The following REIC/Dkk-3 DNA, which is used for treating mesothelioma:
(a) a DNA consisting of the nucleotide sequence shown in SEQ ID NO: 1; or
(b) a DNA hybridizing under stringent conditions to a DNA consisting of a nucleotide sequence complementary to the nucleotide sequence shown in SEQ ID NO: 1 and encoding a protein having apoptosis-inducing activity and IL-7 production accelerating activity in cells.

[23] The REIC/Dkk-3 DNA according to [22], wherein the mesothelioma is pleuramesothelioma.

[24] The REIC/Dkk-3 DNA according to [23], which is administered intrapleurally.

[25] The REIC/Dkk-3 DNA according to any one of [22] to [24], which induces apoptosis in tumor cells and potentiates the antitumor immunity of normal cells.

[26] A vector comprising the REIC/Dkk-3 DNA of [22], which is used for treating mesothelioma.

[27] The vector comprising the REIC/Dkk-3 DNA according to [26], wherein the vector is an adenovirus vector.

[28] The vector comprising REIC/Dkk-3 DNA according to [26] or [27], wherein the mesothelioma is pleuramesothelioma.

[29] The vector comprising REIC/Dkk-3 DNA according to [28], which is administered intrapleurally.

[30] The vector comprising REIC/Dkk-3 DNA according to any one of [26] to [29], which induces apoptosis in tumor cells and potentiates the antitumor immunity of normal cells.

[31] The following REIC/Dkk-3 DNA, which is used for immunopotentiation of an animal:
(a) a DNA consisting of the nucleotide sequence shown in SEQ ID NO: 1; or
(b) a DNA hybridizing under stringent conditions to a DNA consisting of a nucleotide sequence complementary to the nucleotide sequence shown in SEQ ID NO: 1 and encoding a protein having apoptosis-inducing activity and IL-7 production accelerating activity in cells.

[32] The vector comprising REIC/Dkk-3 DNA according to [31], which is used for immunopotentiation of an animal.

[33] The vector comprising REIC/Dkk-3 DNA according to [32], wherein the vector is an adenovirus vector.

This description includes part or all of the contents as disclosed in the Description and/or drawings of Japanese Patent Application No. 2008-196857, which is a priority document of the present application.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

BEST MODE OF CARRYING OUT THE INVENTION

Figure 1:
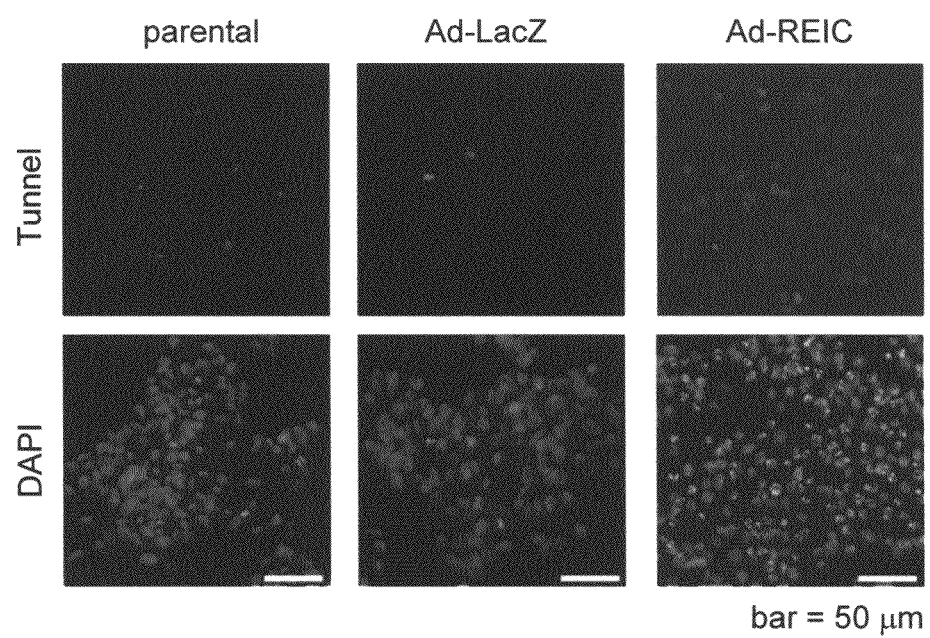
FIG. 1 shows apoptosis induction in 211H cells by REIC/Dkk-3.

The present invention will be described in detail as follows.

The mesothelioma therapeutic agent according to the present invention comprises REIC/Dkk-3 DNA or a vector comprising the DNA as an active ingredient.

The nucleotide sequence of REIC/Dkk-3 DNA is shown in SEQ ID NO: 1. Also, the amino acid sequence of REIC/Dkk-3 protein encoded by REIC/Dkk-3 DNA is shown in SEQ ID NO: 2.

The protein encoded by REIC/Dkk-3 DNA contained in the mesothelioma therapeutic agent of the present invention: has the amino acid sequence shown in SEQ ID NO: 2 or an amino acid sequence that is substantially the same as the amino acid sequence shown in SEQ ID NO: 2; and has apoptosis-inducing activity for tumor cells and activity of accelerating production of interleukin 7 (IL-7) by cells. Examples of such substantially the same amino acid sequence include: an amino acid sequence that has a substitution, a deletion, and/or an addition of one, a plurality of, or several (1 to 10, preferably 1 to 5, further preferably 1 or 2) amino acids with respect to the amino acid sequence shown in SEQ ID NO: 2; or an amino acid sequence having at least 85% or more, preferably 90% or more, further preferably 95% or more, and particularly preferably 97% or more identity with the amino acid sequence shown in SEQ ID NO: 2 as calculated using BLAST (Basic Local Alignment Search Tool at the National Center for Biological Information (NCBI)) or the like (for example, using default; that is, initially set parameters).

The protein encoded by REIC/Dkk-3 DNA can be obtained by chemical synthesis based on the sequence information of SEQ ID NO: 1 or SEQ ID NO: 2. Also, the protein encoded by REIC/Dkk-3 DNA can be obtained as a recombinant REIC/Dkk-3 protein by genetic engineering techniques. The protein encoded by REIC/Dkk-3 DNA can further be obtained according to description in the WO01/038523 publication.

REIC/Dkk-3 DNA contained in the mesothelioma therapeutic agent of the present invention is:

a DNA hybridizing under stringent conditions to a DNA having a nucleotide sequence complementary to the nucleotide sequence shown in SEQ ID NO: 1;

a DNA having at least 85% or more, preferably 90% or more, further preferably 95% or more, particularly preferably 97% or more identity with the nucleotide sequence shown in SEQ ID NO: 1 as calculated using BLAST (Basic Local Alignment Search Tool at the National Center for Biological Information (NCBI)) or the like (for example, using default; that is, initially set parameters); or a DNA encoding a protein consisting of an amino acid sequence that has substitution, deletion, and/or addition of one, a plurality of, or several (1 to 10, preferably 1 to 5, further preferably 1 or 2) amino acids with respect to the amino acid sequence of the protein encoded by the above DNA, which encodes a protein having apoptosis-inducing activity for tumor cells and activity of accelerating interleukin 7 (IL-7) production in cells. The term "stringent conditions" used herein refers to, for example, stringent conditions of about 1×SSC, 0.1% SDS, and 37° C., more stringent conditions of about 0.5×SSC, 0.1% SDS, and 42° C., or even more stringent conditions of about 0.2×SSC, 0.1% SDS, and 65° C. Moreover, REIC/Dkk-3 DNA contained in the mesothelioma therapeutic agent of the present invention is a DNA encoding the protein shown in SEQ ID NO: 2.

REIC/Dkk-3 DNA can be obtained from human cells, human tissues and the like based on the sequence information of SEQ ID NO: 1. Also, REIC/Dkk-3 DNA can also be obtained according to description of WO01/038523.

Furthermore, the present invention also encompasses a vector comprising REIC/Dkk-3 DNA. The vector is introduced into a test subject and then the REIC/Dkk-3 protein is expressed in vivo in the test subject, so that therapeutic effects can be exerted to mesothelioma.

Transfection of a gene of interest (DNA) into a test subject upon gene therapy can be carried out in accordance with known methods. Examples of a method for gene transfection into a test subject include a method using a viral vector and a method using a nonviral vector. A variety of such methods have been known to the public (Experimental Medicine (additional volume), Basic Techniques for Gene Therapy (*Idenshi Chiryo no Kiso Gijutsu*), Yodosha Co., Ltd., 1996; Experimental Medicine (additional volume), Experimental Methods for Gene Transfection & Expression Analysis (*Idenshi Donyu & Hatsugen Kaiseki Jikkenho*), Yodosha Co., Ltd., 1997; "Handbook for Gene Therapy Research and Development" (*Idenshi Chiryo Kaihatsu Kenkyu* Handbook), edited by the Japan Society of Gene Therapy, NTS Inc., 1999).

Methods using adenovirus, adeno-associated virus (AAV), retrovirus, and the like as viral vectors for gene transfection are typically employed. Gene transfection into cells can be carried out by introducing a gene of interest into a DNA or RNA virus such as detoxicated retrovirus, herpesvirus, vaccinia virus, poxvirus, poliovirus, Sindbis virus, Sendai virus, SV40, or human immunodeficiency virus (HIV) and allowing the obtained recombinant virus to infect cells.

When the gene according to the present invention is used for a gene therapy using a virus, an adenovirus vector is preferably used. For instance, adenovirus vectors are characterized in that: (1) gene transfection can be performed in a variety of cells; (2) gene transfection can be efficiently performed even for cells in growth arrest; (3) they can be concentrated by centrifugation such that a virus with a high titer (10 to 11 PFU/ml or more) can be obtained; and (4) they are appropriate for use in direct gene transfection into in vivo tissue cells. As an adenovirus vector used for gene therapy, the following vectors have been developed: a second generation adenovirus vector (Lieber, A., et al., J. Virol., 70, 8944, 1996; Mizuguchi, H. & Kay, M. A., Hum. Gene Ther., 10, 2013, 1999) obtained by deleting the E2 or E4 domain in addition to the E1/E3 domain from a first generation adenovirus vector lacking the E1/E3 domain (Miyake, S., et al., Proc. Natl. Acad. Sci. U.S.A., 93, 1320, 1996); and a third generation adenovirus vector (Steinwaerder, D. S. et al., J. Virol., 73, 9303, 1999) almost completely lacking the adenovirus genome (GUTLESS). However, for transfection of the gene according to the present invention, any adenovirus vector may be used without particular limitation. Further, use of an adeno-AAV hybrid vector having the ability to cause incorporation in the AAV chromosome (Recchia, A. et al., Proc. Natl. Acad. Sci. U.S.A., 96, 2615, 1999) and an adenovirus vector that has acquired the ability to cause incorporation in the chromosome with the use of a transposon gene can be applied for long-term gene expression using. In addition, it is possible to impart tissue specificity to an adenovirus vector by inserting a peptide sequence exerting tissue-specific transferability for the H1 loop of an adenovirus fiber (Mizuguchi, H. & Hayakawa, T., Nippon Rinsho, 7, 1544, 2000).

In the present invention, an adenovirus vector comprising REIC/Dkk-3 DNA is referred to as Ad-REIC.

Further, even without the use of the above viruses, it is possible to transfect cells or tissue with a gene of interest using a recombinant expression vector comprising a gene expression vector, such as a plasmid vector incorporated therein. For instance, gene transfection into cells can be performed by a lipofection method, a calcium phosphate coprecipitation method, a DEAE-dextran method, and a DNA direct injection method using a micro glass tube. Furthermore, it is possible to allow a recombinant expression vector to be incorporated into cells by a gene transfection method using internal liposomes, a gene transfection method using electrostatic type liposomes, an HVJ-liposome method, a modified HVJ-liposome method (HVJ-AVE liposome method), a method using an HVJ-E (envelope) vector, a transfection method performed through mediation by a receptor, a method of transferring DNA molecules into cells with carriers (metallic particles) using a particle gun, a method of direct transfection of naked DNA, a transfection method using a variety of polymers, or the like. The expression vector used in such case may be any expression vector as long as it allows in vivo expression of a gene of interest. Examples thereof include expression vectors such as pCAGGS (Gene 108, 193-200 (1991)), pBK-CMV, pcDNA3.1, pZeoSV (Invitrogen Corporation, Stratagene), and pVAX1.

A vector comprising REIC/Dkk-3 DNA may adequately comprise a promoter or enhancer for gene transcription, a polyA signal, a marker gene used for labeling and/or selection of cells transfected with a gene, or the like. Examples of a promoter that can be used in such case include known promoters.

In order to introduce a vector comprising REIC/Dkk-3 DNA of the present invention into a test subject, the following methods or the like may be used: an in vivo method, whereby a gene therapeutic agent is directly introduced into a living body; and an ex vivo method, whereby a specific cell is collected from a human, a gene therapeutic agent is introduced ex vivo into the cell, and the cell is returned into the human body (Nikkei Science, 1994, 4, pp. 20-45; The Pharmaceuticals Monthly, 36(1), 23-48 (1994); Experimental Medicine (additional volume), 12(15), (1994); "Handbook for Gene Therapy Research and Development" (*Idenshi Chiryo Kaihatsu Kenkyu* Handbook), edited by the Japan Society of Gene Therapy, NTS Inc., 1999).

In the present invention, the term "mesothelioma" refers to "malignant mesothelioma." Examples of malignant mesothelioma include pleuramesothelioma, peritoneal mesothelioma, and pericardial mesothelioma. In particular, malignant pleuramesothelioma is preferred.

The mesothelioma therapeutic agent of the present invention induces apoptosis in tumor cells, enhances IL-7-producing capability in normal cells, and activates NK cells, thereby potentiating antitumor immunity. As a result, synergistic therapeutic effects are exerted against malignant mesothelioma based on two actions: apoptosis induction in tumor cells by REIC/Dkk-3; and antitumor immunity of normal cells. Treatment using the mesothelioma therapeutic agent of the present invention can be said as a gene therapy for malignant mesothelioma targeting tumor cells and normal cells.

The present invention encompasses an agent for accelerating IL-7 production by cells, which comprises the above REIC/Dkk-3 DNA or a vector comprising the DNA. Furthermore, the present invention encompasses an antitumor immunostimulant comprising the above REIC/Dkk-3 DNA or vector comprising the DNA.

The mesothelioma therapeutic agent, the agent for accelerating IL-7 production, and the antitumor immunostimulant of the present invention can be administered in various forms. For instance, it can be formed into tablets, capsules, granules, powders, syrups, or the like for oral administration. Alternatively, it can be formed into injections, infusions, suppositories, sprays, eye drops, nasal preparations, adhesive preparations, or the like for parenteral administration.

The mesothelioma therapeutic agent, the agent for accelerating IL-7 production, and the antitumor immunostimulant of the present invention may be topically administered. For instance, the effects thereof can be exerted against pleuramesothelioma when they are administered in the pleural space via catheter or injection, for example.

Preferably, the agent is directly injected in the pleural space once or several times, so that the agent is spread throughout the entire affected intrapleural part.

The mesothelioma therapeutic agent, the agent for accelerating IL-7 production, or the antitumor immunostimulant of the present invention contains a carrier, a diluent, and/or an excipient, which is usually used in the pharmaceutical field. Examples of a carrier and an excipient used for tablets include lactose and magnesium stearate. Examples of aqueous liquid used for injection include physiological saline and isotonic solutions containing glucose or other adjuvants, which may be used in combination with adequate solubilizers, including alcohol, polyalcohol such as propylene glycol, and nonionic surfactants. Examples of an oily liquid that can be used herein include sesame oil and soybean oil. Examples of a solubilizer that may be used in combination include benzyl benzoate and benzyl alcohol.

The dose of the mesothelioma therapeutic agent, the agent for accelerating IL-7 production, or the antitumor immunostimulant of the present invention is determined depending on patient's symptoms, age, body weight, and the like. They may be administered once every several days, several weeks, or several months in an amount ranging from 0.001 mg to 100 mg of the DNA.

Also, when a vector comprising REIC/Dkk-3 DNA is used, $10^7$ to $10^9$ pfu (plaque forming unit) of the vector may be administered, for example.

The present invention is hereafter described in greater detail with reference to the following examples, although the technical scope of the present invention is not limited thereto.

Example 1

Anti-Tumor Effects of REIC/Dkk-3

In this Example, 211H cells, H28 cells, and H2052 cells, which were Hela cells and malignant mesothelioma cells, were used. These cells were obtained from ATCC (American Type Cell Culture Collection). Cells were maintained under conditions of 37° C. and 5% $CO_2$ using RPMI1640 medium (GIBCO) supplemented with 10% dialysis fetal calf serum (FBS), 2 mM glutamine, 100 units/ml penicillin, and 100 µg/ml streptomycin.

An adenovirus vector (Ad-REIC) comprising REIC/Dkk-3 DNA was constructed by the following method. Specifically, full-length REIC/Dkk-3 cDNA was introduced into a pAx-CAwt cosmid vector and then transferred to an adenovirus vector by the COS-TPC method (Takara Bio) (Abarzua F et al. Cancer Res 2005; 65: 9617-9622). An adenovirus vector (Ad-LacZ) comprising a LacZ gene was used as a control.

211H transfectant cells (211H/Luc) stably expressing a luciferase gene were prepared by introducing a pIRES-piro3-luciferase plasmid into 211H cells according to the description of Kashiwakura Y. et al., Circulation 1003; 107: 1078-81.

(1) JNK-Dependent Apoptosis Induction in Mesothelioma Cells by REIC/DKK-3

Tunnel [cell death (apoptosis)] assay was performed by the following method. Specifically, to examine in vitro cell death induction, cells were seeded in a 6-well flat bottom plate and then cultured for 24 hours. Cells were treated with Ad-LacZ and Ad-REIC at various MOIs (multiplicities of infection) in serum free medium for 2 hours and then the medium was exchanged with fresh complete medium. After 48 hours of incubation, TUNEL (terminal deoxynucleotidyltransferase-mediated UTP end labeling) assay was performed using an in situ Cell Death Detection Fluorescein kit (Roche Diagnostics), and then apoptosis was evaluated. Specifically, cells having GFP-positive nuclei were determined to be apoptosis cells, and the number of apoptosis-positive cells per 100 cells (DAPI-positive nuclei) was determined. Cells confirmed to have undergone cell death in 3 to 5 different visual fields were counted under a microscope.

To detect in vivo cells for which cell death had been confirmed, TUNEL assay was carried out using a Fluorescein In Situ Cell Detection Kit (Roche). Specifically, tumor tissues were cut into sections and each section was added into an OCT compound and then rapidly frozen in liquid nitrogen. Each frozen section sample (10 µm) was fixed with methanol at room temperature for 30 minutes, washed, impregnated with PBS containing 0.1% Triton X-100, and then stained with a TUNEL reaction mixture.

Figure 2:
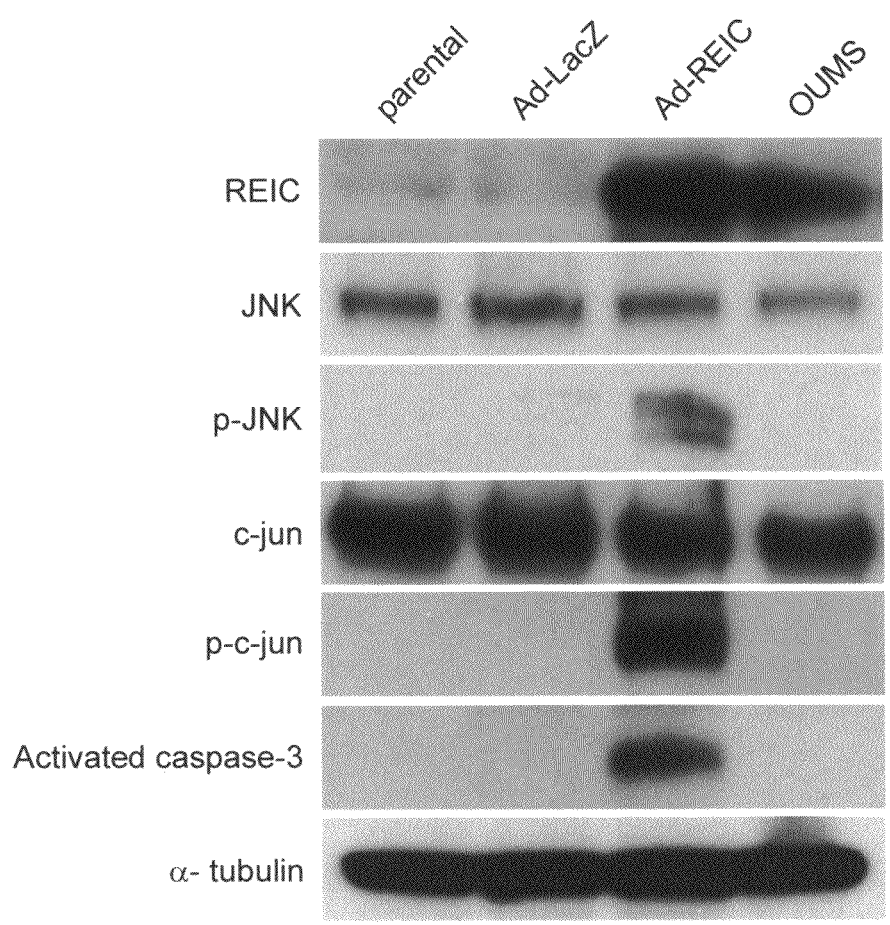
FIG. 2 shows acceleration of the expression of pJNK, pc-jun, and activated caspase 3 in 211H cells by REIC/Dkk-3.

Western blot analysis was conducted using the antibodies against proteins shown in FIG. 2, such as an anti-human REIC/Dkk-3 antibody.

211H cells (human malignant mesothelioma cells) were infected with Ad-LacZ or Ad-REIC (20MOI). Apoptosis was evaluated after 48 hours. FIG. 1 shows the results. Cells having GFP-positive nuclei were apoptotic cells. As shown in FIG. 1, Ad-REIC-infected cells clearly included many apoptotic cells.

FIG. 2 shows the results of Western blot analysis on cells used herein. As shown in FIG. 2, pJNK expression, pc-jun expression, and active caspase-3 expression were clearly increased in Ad-REIC-infected cells. Specifically, it was demonstrated that apoptosis took place through mediation of INK activity due to Ad-REIC infection.

Figure 3:
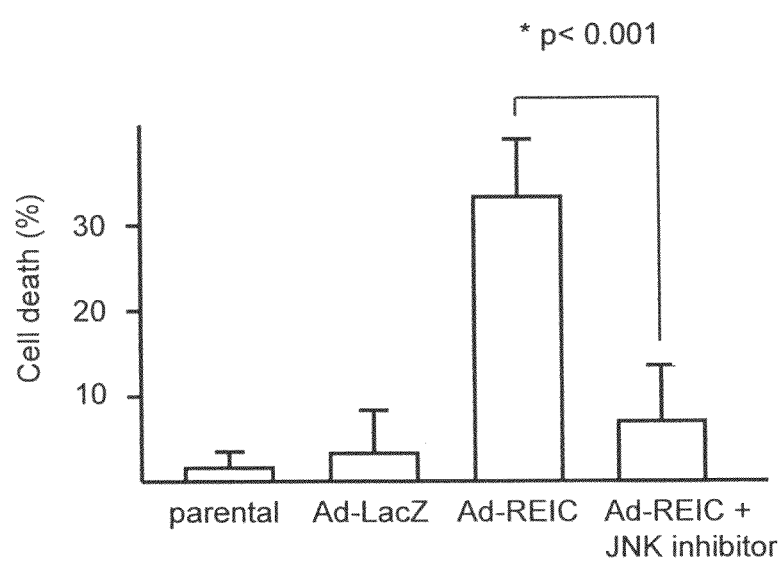
FIG. 3 shows suppression of apoptosis (induced by REIC/Dkk-3) in 211H cells by a JNK inhibitor.

Furthermore, apoptosis assay was performed after addition of a JNK inhibitor. FIG. 3 shows the results. Ad-REIC-induced apoptosis was significantly suppressed by the JNK inhibitor. Therefore, it was demonstrated that Ad-REIC-induced apoptosis in 211H cells took place in a INK-dependent manner.

(2) Decreased Id-1 Expression by REIC/Dkk-3

The following infection experiment was conducted to examine in vitro changes in the expression of various proteins via Ad-REIC infection. Firstly, cells were seeded in a 6-well flat bottom plate and then cultured for 24 hours. Cells were treated with Ad-LacZ and Ad-REIC at 20 MOI (multiplicity of infection) in serum free medium for 2 hours and then the medium was exchanged with fresh complete medium. After 48 hours of incubation, proteins were collected and then subjected to Western blot.

Figure 4:
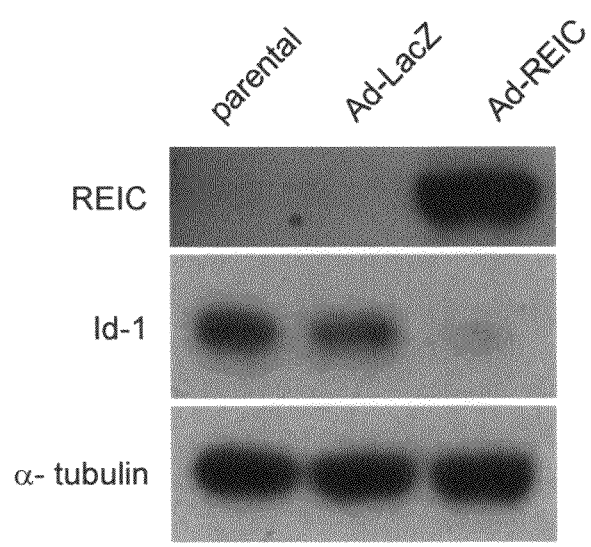
FIG. 4 shows suppression of Id-1 expression in 211H cells by REIC/Dkk-3.

FIG. 4 shows the results of Western blot analysis of Id-1 (Inhibition of differentiation-1). As shown in FIG. 4, at 48 hours after Ad-REIC infection, Id-1 expression had clearly decreased in 211H cells.

Next, the following infection experiment was conducted and then apoptosis was analyzed to examine the effects of Id-1 re-expression on Ad-REIC-induced apoptosis. Cells were seeded in a 6-well flat bottom plate and then cultured for 24 hours. Cells were treated with Ad-LacZ, Ad-REIC, and Ad-Id-1 (Id-1 adenovirus) at the following MOIs in serum free medium for 2 hours Well1-Ad-REIC 20 MOI, Well2-Ad-REIC 20 MOI+Ad-LacZ 10 MOI, and Well3-Ad-REIC 20 MOI+Ad-Id-1 10 MOI.

Figure 5:
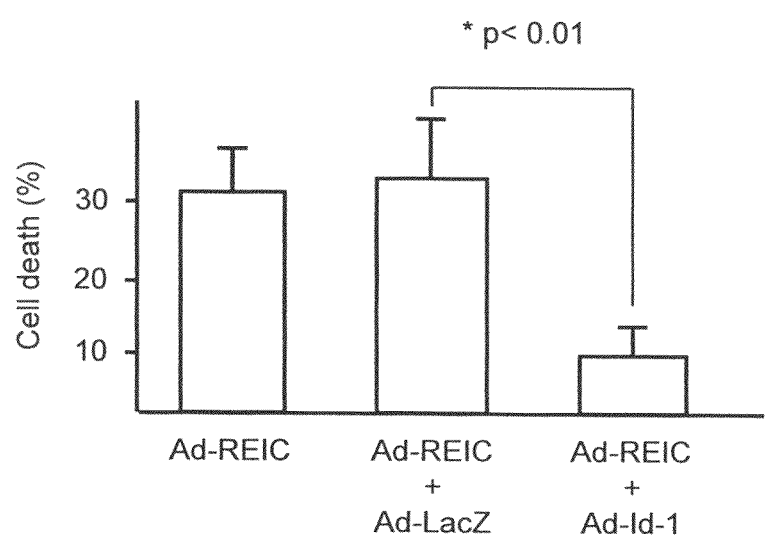
FIG. 5 shows a decrease in apoptosis (induced by REIC/Dkk-3) in 211H cells by forced expression of Id-1.

After exchange with fresh complete medium, incubation was performed for 48 hours and then apoptosis was evaluated by TUNEL assay. As shown in FIG. 5, at 48 hours after infection, Ad-REIC-induced apoptosis had clearly decreased as a result of forced expression of Id-1. This demonstrates that Ad-REIC-induced apoptosis depends on a decrease in Id-1.

Figure 6:
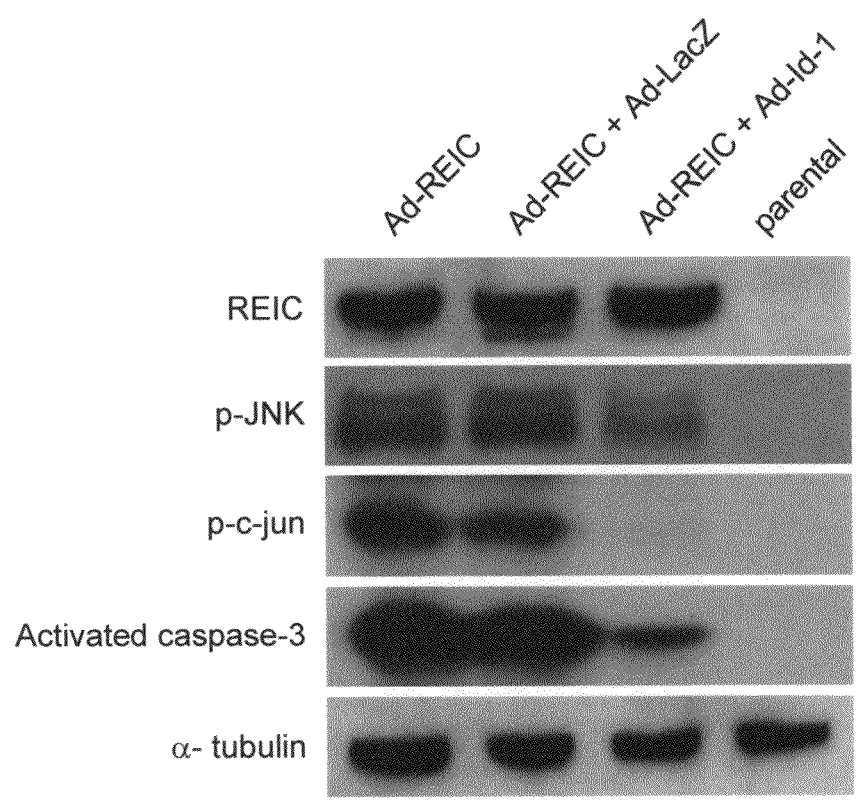
FIG. 6 shows suppression of the expression of pJNK, pc-jun, and activated caspase 3 (accelerated by REIC/Dkk-3 in 211H cells) by forced expression of Id-1.

FIG. 6 shows the results of Western blot analysis for parental cells (untreated 211H cells) and cells used in FIG. 5. As shown in FIG. 6, forced expression of Id-1 suppressed increases in pJNK expression, pc-jun expression, and active caspase-3 expression due to induction via Ad-REIC. Specifically, it was demonstrated that JNK activation, which is a fundamental mechanism of Ad-REIC-induced apoptosis, was inhibited by forced expression of Id-1. Hence, it was considered that "a decrease in Id-1 expression due to Ad-REIC infection accelerates Ad-REIC-induced apoptosis."

(3) Examination Using H28 Cell and H2052 Cell

Figure 7:
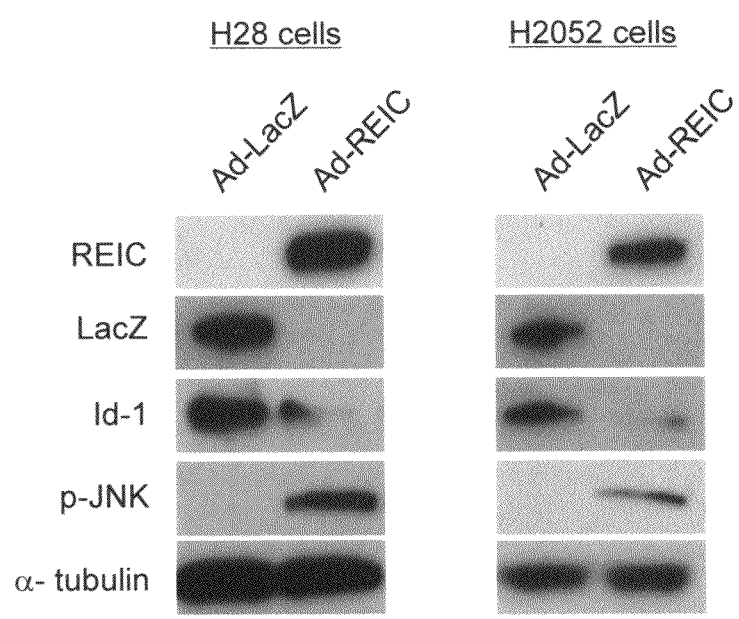
FIG. 7 shows apoptosis induction in H28 cells and H2052 cells by REIC/Dkk-3.
Figure 8:
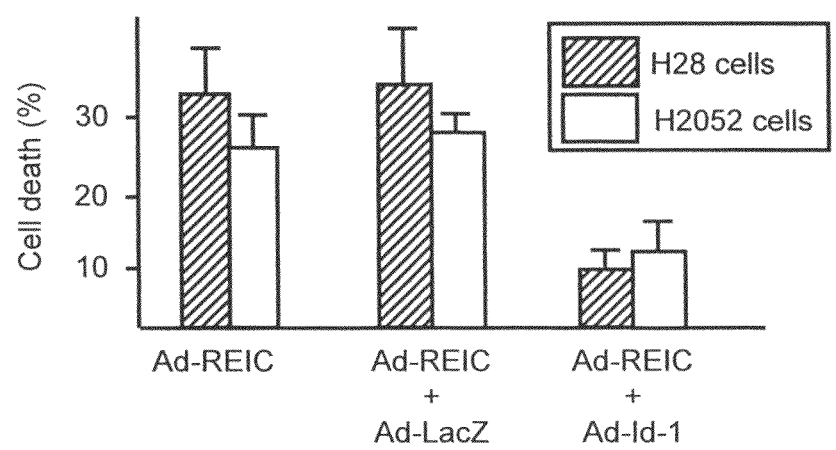
FIG. 8 shows decreases in apoptosis (induced by REIC/Dkk-3) in H28 cells and H2052 cells by forced expression of Id-1.

Ad-REIC-induced apoptosis was examined in a manner similar to that in (1) and (2) above using malignant mesothelioma cells (H28 and H2052). As shown in FIG. 7, decreases in Id-1 and phosphorylation (activation) of JNK due to Ad-REIC infection were observed in H28 and H2052, similarly to the case of 211H. Moreover, as shown in FIG. 8, Ad-REIC-induced apoptosis was suppressed by forced expression of Id-1. Specifically, the mechanism of Ad-REIC infection→decrease in Id-1→phosphorylation (activation) of JNK→apoptosis was also observed in other malignant mesothelioma cells.

(4) Examination (No. 1) Using Malignant Mesothelioma Model Mouse $2.0 \times 10^6$ 211H/Luc in 100-μL PBS was administered via the right thoracic wall to 8-week-old BALB/C nude mice (obtained from SLC), so that sympatric malignant mesothelioma model mice were produced. At 1 week after administration, Ad-REIC and Ad-lacZ in 100-μL PBS ($4.0 \times 10^8$ plaque-forming units) were administered into the pleural space through the same site as the site through which the above cells had been administered. PBS in the same amount as that of the 100-μL PBS was administered as a negative control. Luminescence was measured every 5 days using an IVIS imaging system (in vivo luciferase imaging system) for 20 days after administration. Moreover, the death of mice was monitored. Tumor sizes and the lower parts thereof were evaluated on day 10 using other treatment groups.

Figure 9A:
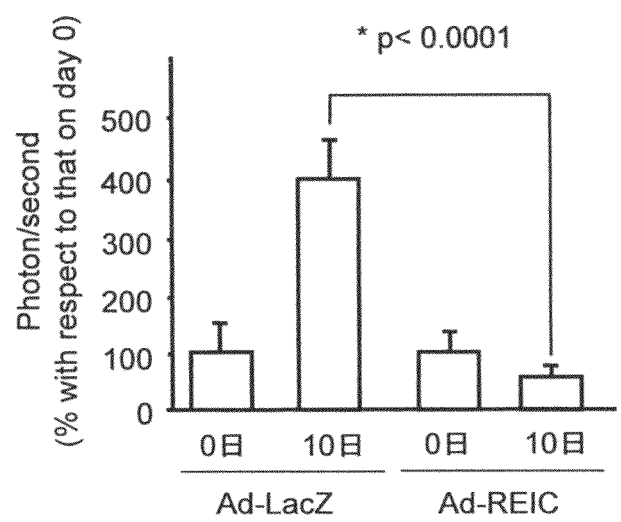
FIG. 9a shows anti-tumor effects of REIC/Dkk-3 in nude mice in which 211H/Luc cells were implanted.
Figure 9B:
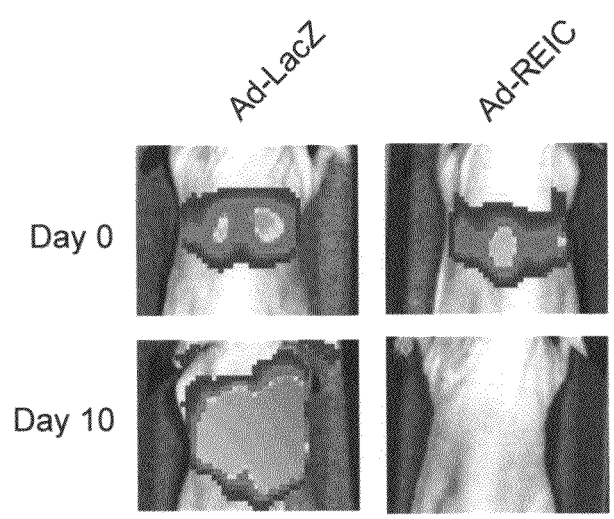
FIG. 9b shows IVIS images showing anti-tumor effects of REIC/Dkk-3 in nude mice in which 211H/Luc cells were implanted.

FIG. 9a shows quantitative determination (unit: photon/sec) of the number of 211H/Luc cells (=tumor volume) via IVIS. Compared with the result obtained before treatment (Day 0), tumor volumes were significantly lowered by Day 10 in the Ad-REIC treatment group. FIG. 9b shows IVIS images corresponding to FIG. 9a.

Figure 9C:
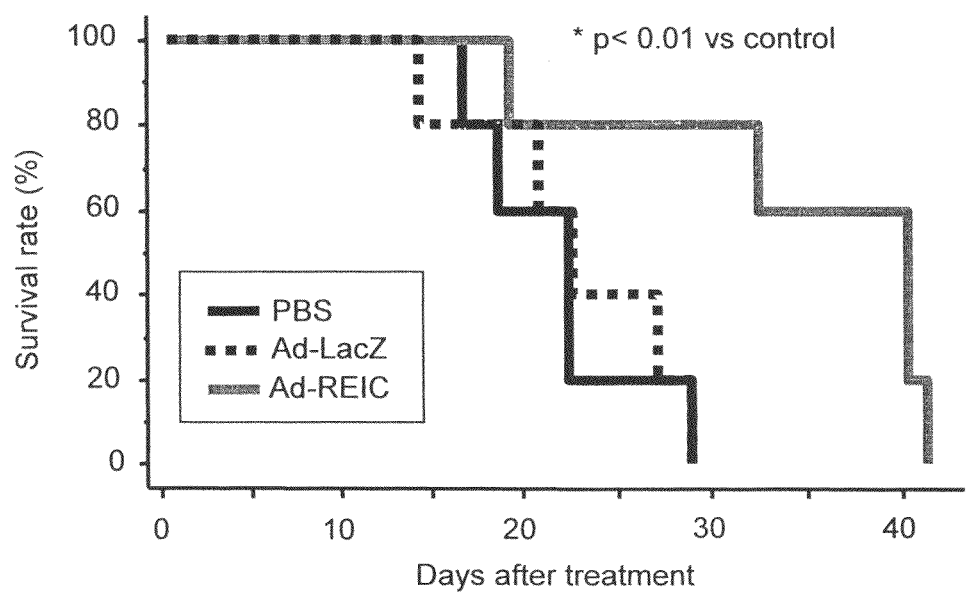
FIG. 9c shows the survival rate of each nude mouse when REIC/Dkk-3 was administered to nude mice in which 211H/Luc cells had been implanted.

FIG. 9c shows survival rate curves. As shown in FIG. 9c, compared with the control group, the survival rate was clearly improved in the Ad-REIC treatment group. It was considered based on the above results that intrapleural administration of Ad-REIC has significant therapeutic effects on malignant mesothelioma.

(5) Examination (No. 2) Using Malignant Mesothelioma Model Mouse

Ad-LacZ-infected mice used in (4) above were dissected on day 7 after infection, tumors were separated from normal tissues, and then LacZ transgene expression within tumors and normal pleura was analyzed by LacZ staining. The method for LacZ staining is as follows. After 18 hours of fixation at 37° C. using PBS as a fixative (pH 8.0) (1% formaldehyde (37% and 2.7 ml), 0.2% glutaraldehyde (25% and 0.8 ml), 2 mM MgCl$_2$ 1M (0.2 ml), and 5 mM EGTA (200 mM and 2.5 ml)), incubation was performed for 12 hours at room temperature while protecting the samples from light exposure using a lacZ stain solution (5 mM potassium ferricyanide (100 mM and 2.5 ml), 5 mM potassium ferrocyanide (100 mM and 2.5 ml), 2 mM MgCl$_2$ (1 M and 0.1 ml), 0.01% sodium deoxycholate (10% and 0.05 ml), 0.02% NP40 (10% and 0.1 ml), and 1 mg/ml X-gal (50 mg/ml and 1 ml) in 50 ml of PBS). Thus, LacZ expression was analyzed.

Figure 10A:
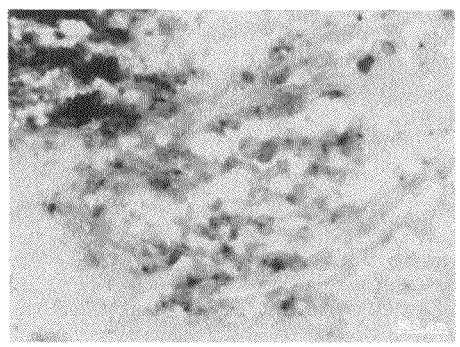
FIG. 10a shows REIC/Dkk-3 expression after intratumoral introduction thereof.

FIG. 10a shows the result of analyzing intratumor transgene expression in the Ad-LacZ group via LacZ staining. As shown in FIG. 10a, gene transfer was confirmed in about 50% of intratumor cells, but no gene transfer was confirmed in the other cells. In spite of such result, significant anti-tumor effects were observed. Hence, it was considered that intrapleural administration of Ad-REIC has some effects of anti-tumor immunity.

Figure 10B:
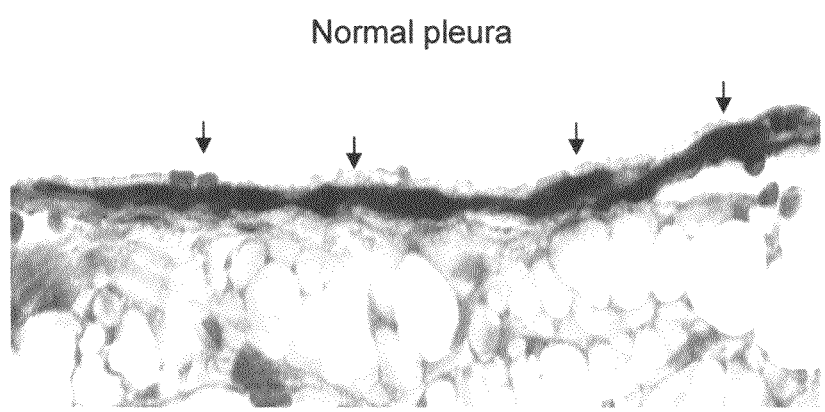
FIG. 10b shows REIC/Dkk-3 expression in normal pleura.

FIG. 10b shows the result of analyzing transgene expression in normal pleura of the Ad-LacZ group by LacZ staining. Gene expression was clearly confirmed in normal visceral pleura (black arrows). It was strongly suggested based on this finding that strong expression of REIC in normal pleura induced some effects of antitumor immunity.

Example 2

Acceleration of IL-7 Expression by REIC/Dkk-3

Antitumor immunity of Ad-REIC was analyzed using normal human fibroblasts. OUMS24 cells were used as normal human fibroblasts. They were established by the present inventors (Bai L et al. Int J Cancer 1993; 53: 451-456), for example.

Figure 11:
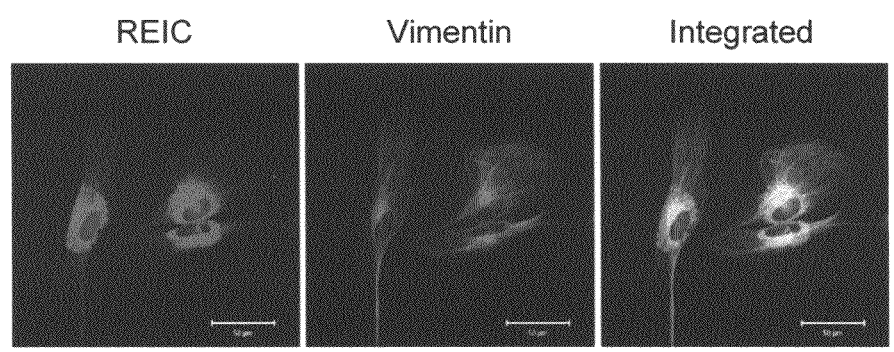
FIG. 11 shows antitumor immunological effects of REIC/Dkk-3 in normal cells.

The above cells were treated with Ad-REIC at 20 MOI for 48 hours, so that the cells were infected with Ad-REIC. FIG. 11 shows the results of immunostaining when normal fibroblasts were infected with Ad-REIC. The presence of forcedly expressed REIC within cells (endoplasmic reticulum) was confirmed.

Figure 12:
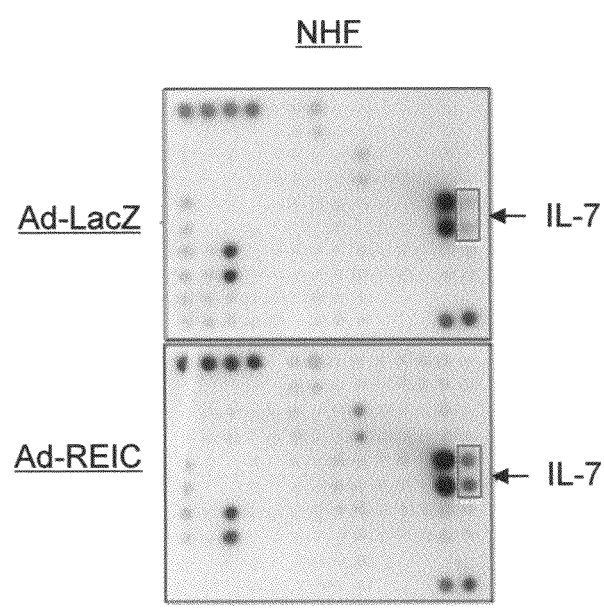
FIG. 12 shows the effects of enhancing IL-7 production in normal cells by REIC/Dkk-3 (cytokine array analysis).

Cytokines in a culture supernatant obtained when normal fibroblasts were infected with Ad-REIC were analyzed using a cytokine array. As a cytokine array, RayBio Human Cytokine Antibody Array VI & 6.1 (RayBiotech, Norcross, Ga.) was used. FIG. 12 shows the results. As shown in FIG. 12, increases in IL-7 concentration were confirmed (within squares in FIG. 12).

Furthermore, Northern blot analysis was conducted using Ad-REIC-infected normal fibroblasts. Total RNA was isolated by an acid guanidine thiocyanate phenol-chloroform extraction method. 20 μg of RNA was fractionated in 1.0% agarose gel and then transferred to a nylon membrane (Nytran plus nylon membrane, GE Healthcare Bio-Sciences). A human IL-7 gene fragment was used as a probe.

Figure 13:
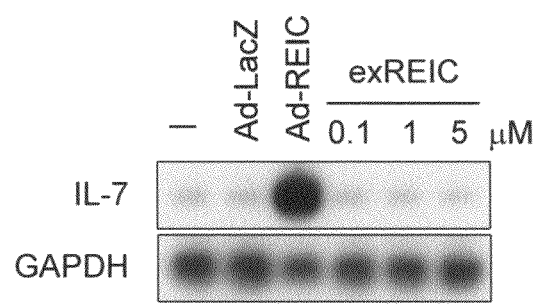
FIG. 13 shows the effects of enhancing IL-7 production in normal cells by REIC/Dkk-3 (Northern blot analysis).

FIG. 13 shows the results of Northern blot analysis for Ad-REIC-infected normal fibroblasts. In FIG. 13, exREIC indicates a recombinant REIC protein added. As shown in FIG. 13, it was confirmed that IL-7 mRNA expression had been clearly enhanced in Ad-REIC-infected normal fibroblasts.

Figure 14:
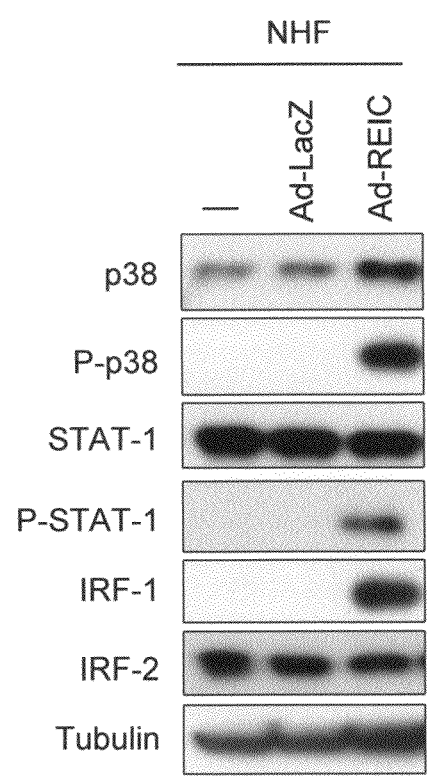
FIG. 14 shows the mechanism of enhancement of IL-7 production by REIC/Dkk-3.

Moreover, Western blot analysis was conducted using antibodies against proteins, as shown in FIG. 14. The mechanism for enhancement of IL-7 expression via REIC/Dkk-3 was analyzed. IL-7 transfer was activated by IRF-1 and IRF-2, but IRF-1 expression enhanced by infection with Ad-REIC was confirmed in fibroblasts (IRF-2 expression was always observed). As the mechanism of enhancement of IRF-1 expression, JNK activation→p38 activation→STAT-1 activation was demonstrated.

It was confirmed based on the results of this Example that infection of normal cells with Ad-REIC results in enhanced IL-7 production. IL-7 is known to activate NK (Natual Killer) cells and to potentiate antitumor immunity. It is considered that also in normal pleural cells, infection with Ad-REIC enhances IL-7 production, so as to potentiate antitumor immunity mediated by NK cells.

Figure 15:
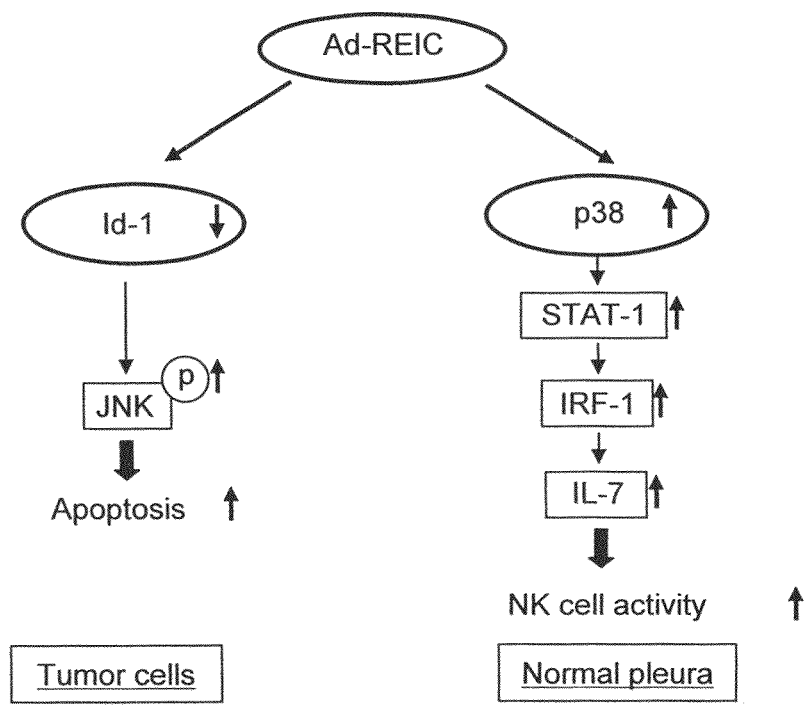
FIG. 15 shows the molecular biological mechanism of anti-malignant mesothelioma effects induced by REIC/Dkk-3.

FIG. 15 shows the molecular biological mechanism of the anti-malignant mesothelioma effects induced by intrapleural administration of Ad-REIC. As shown in FIG. 15, there are two possible pathways: suppression of Id-1 expression; and p38 activation. The former pathway induces apoptosis in tumor cells and the latter pathway induces enhanced IL-7 production in normal pleural cells, thereby inducing NK cell activation.

INDUSTRIAL APPLICABILITY

As described in the Examples, intrapleural administration (single dose) of an adenovirus vector (Ad-REIC) comprising REIC/Dkk-3 DNA to sympatric malignant mesothelioma model mice resulted in significant reduction in tumor volume and improvement in survival rate observed. In sympatric malignant mesothelioma model mice, intrapleural administration of Ad-REIC (single dose) resulted in significant reduction in tumor volume and improvement in survival rate. Also, no clear adverse reaction was observed. As described above, intrapleural administration of Ad-REIC is an extremely effective therapy for malignant mesothelioma. Also, as demonstrated by the Examples, JNK-dependent apoptosis is due to decreased expression of Id-1 (inhibition of differentiation-1) involved in cell growth and the like. Id-1 is strongly expressed in many types of cancer and involved in cell growth and drug resistance. Thus, Ad-REIC can exert anti-tumor effects against a broad range of cancer types. Intrapleural administration of Ad-REIC leads to enhancement in IL-7 production in normal pleura and activates antitumor immunity mainly of NK cells, exerting extremely good therapeutic effects in addition to Ad-REIC's own apoptosis-inducing effects on tumor cells.

All publications, patents, and patent applications cited herein are incorporated herein by reference in their entirety.

The invention claimed is:

1. A method for potentiating the antitumor immunity against pleural mesothelioma in an animal, comprising intrapleurally administering a REIC/Dkk-3 DNA consisting of the nucleotide sequence shown in SEQ ID NO:1 or a vector comprising the DNA to the animal by enhancing interleukin 7-producing capability in normal pleural cells.

2. The method for potentiating antitumor immunity according to claim 1, wherein the vector is an adenovirus vector.

3. A method for potentiating the antitumor immunity against animal cells of pleural mesothelioma in an animal, comprising intrapleurally administering a REIC/Dkk-3 DNA consisting of the nucleotide sequence shown in SEQ ID NO:1 or a vector comprising the REIC/Dkk-3 DNA for uptake by normal pleural cells in the animal whereby interleukin 7-producing capability is increased in the normal pleural animal cells.

* * * * *